(12) United States Patent
Sweetser

(10) Patent No.: US 6,702,793 B1
(45) Date of Patent: Mar. 9, 2004

(54) FEMALE URINE COLLECTION DEVICE

(76) Inventor: Kathleen A. Sweetser, 69 Action Rd., Westford, MA (US) 01886

( * ) Notice: Subject to any disclaimer, the term of this patent is extended or adjusted under 35 U.S.C. 154(b) by 285 days.

(21) Appl. No.: 09/860,323

(22) Filed: May 18, 2001

(51) Int. Cl.[7] ............................................. A61M 1/00
(52) U.S. Cl. ................... 604/327; 604/329; 604/355; 604/347
(58) Field of Search ................. 604/327, 328, 604/329, 330, 331, 349, 317, 355, 347

(56) References Cited

U.S. PATENT DOCUMENTS

| | | | |
|---|---|---|---|
| 3,556,102 A | * | 1/1971 | Davis .......................... 604/329 |
| 3,872,868 A | * | 3/1975 | Kline .......................... 604/403 |
| 4,057,062 A |   | 11/1977 | Lavigne |
| 4,496,355 A | * | 1/1985 | Hall et al. ................... 604/327 |
| 4,795,449 A |   | 1/1989 | Schneider et al. |
| 4,820,291 A | * | 4/1989 | Terauchi et al. ............. 604/349 |
| 4,889,533 A | * | 12/1989 | Beecher ...................... 604/330 |
| 4,904,248 A | * | 2/1990 | Vaillancourt ................ 604/329 |
| 5,049,144 A | * | 9/1991 | Payton ........................ 604/329 |
| 5,053,027 A |   | 10/1991 | Manfredi |
| 5,295,983 A | * | 3/1994 | Kubo .......................... 604/329 |
| 5,411,495 A |   | 5/1995 | Willingham |
| 5,735,835 A | * | 4/1998 | Holland ....................... 604/331 |
| 5,792,132 A | * | 8/1998 | Garcia ..................... 604/385.01 |
| D406,644 S |   | 3/1999 | Keppler |
| 5,919,146 A | * | 7/1999 | Propp .......................... 600/577 |
| 5,957,904 A |   | 9/1999 | Holland |
| 6,151,721 A | * | 11/2000 | Whitfield ..................... 4/144.1 |
| 6,375,028 B1 | * | 4/2002 | Smith ....................... 220/258.1 |

* cited by examiner

Primary Examiner—Weilun Lo
Assistant Examiner—Michele Kidwell

(57) ABSTRACT

A female urine collection device for allowing physically-disabled females who cannot get to a restroom to urinate. The female urine collection device includes a receiver member being adapted to be positioned between legs of a female person; and also includes an absorbent material being removably disposed upon the receiver member; and further includes an elongate flexible tubular member being connected to the receiver member; and also includes a urine collection member being connected to the elongate flexible tubular member.

7 Claims, 2 Drawing Sheets

FEMALE URINE COLLECTION DEVICE

BACKGROUND OF THE INVENTION

1. Field of the Invention

The present invention relates to a urine collection device and more particularly pertains to a new female urine collection device for allowing physically-disabled females who cannot get to a restroom to urinate.

2. Description of the Prior Art

The use of a urine collection device is known in the prior art. More specifically, a urine collection device heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,957,904; 4,795,449; 5,411,495; 4,057,062; 5,053,027; and Des. 406,644.

While these devices fulfill their respective, particular objectives and requirements, the aforementioned patents do not disclose a new female urine collection device. The inventive device includes a receiver member being adapted to be positioned between legs of a female person; and also includes an absorbent material being removably disposed upon the receiver member; and further includes an elongate flexible tubular member being connected to the receiver member; and also includes a urine collection member being connected to the elongate flexible tubular member.

In these respects, the female urine collection device according to the present invention substantially departs from the conventional concepts and designs of the prior art, and in so doing provides an apparatus primarily developed for the purpose of allowing physically-disabled females who cannot get to a restroom to urinate.

SUMMARY OF THE INVENTION

In view of the foregoing disadvantages inherent in the known types of urine collection device now present in the prior art, the present invention provides a new female urine collection device construction wherein the same can be utilized for allowing physically-disabled females who cannot get to a restroom to urinate.

The general purpose of the present invention, which will be described subsequently in greater detail, is to provide a new female urine collection device which has many of the advantages of the urine collection device mentioned heretofore and many novel features that result in a new female urine collection device which is not anticipated, rendered obvious, suggested, or even implied by any of the prior art urine collection device, either alone or in any combination thereof.

To attain this, the present invention generally comprises a receiver member being adapted to be positioned between legs of a female person; and also includes an absorbent material being removably disposed upon the receiver member; and further includes an elongate flexible tubular member being connected to the receiver member; and also includes a urine collection member being connected to the elongate flexible tubular member.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new female urine collection device which has many of the advantages of the urine collection device mentioned heretofore and many novel features that result in a new female urine collection device which is not anticipated, rendered obvious, suggested, or even implied by any of the prior art urine collection device, either alone or in any combination thereof.

It is another object of the present invention to provide a new female urine collection device which may be easily and efficiently manufactured and marketed.

It is a further object of the present invention to provide a new female urine collection device which is of a durable and reliable construction.

An even further object of the present invention is to provide a new female urine collection device which is susceptible of a low cost of manufacture with regard to both materials and labor, and which accordingly is then susceptible of low prices of sale to the consuming public, thereby making such female urine collection device economically available to the buying public.

Still yet another object of the present invention is to provide a new female urine collection device which provides in the apparatuses and methods of the prior art some of the advantages thereof, while simultaneously overcoming some of the disadvantages normally associated therewith.

Still another object of the present invention is to provide a new female urine collection device for allowing physically-disabled females who cannot get to a restroom to urinate.

Yet another object of the present invention is to provide a new female urine collection device which includes a receiver member being adapted to be positioned between legs of a female person; and also includes an absorbent material being removably disposed upon the receiver member; and further includes an elongate flexible tubular member being connected to the receiver member; and also includes a urine collection member being connected to the elongate flexible tubular member.

Still yet another object of the present invention is to provide a new female urine collection device that is easy and convenient to use.

Even still another object of the present invention is to provide a new female urine collection device that reduces the invasive procedures of physically-disabled females when they have to urinate.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
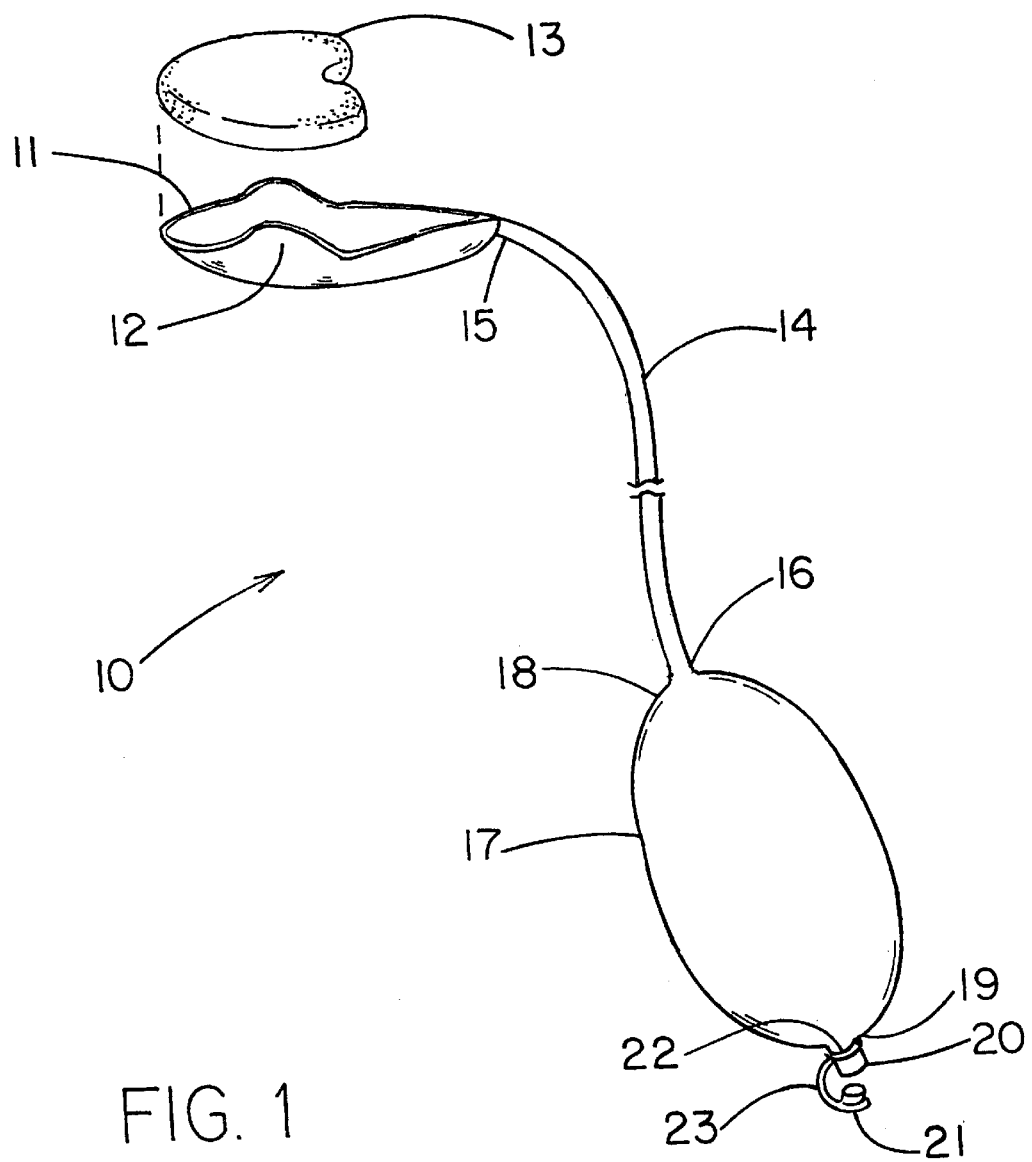
FIG. 1 is an exploded perspective view of a new female urine collection device according to the present invention.
Figure 2:
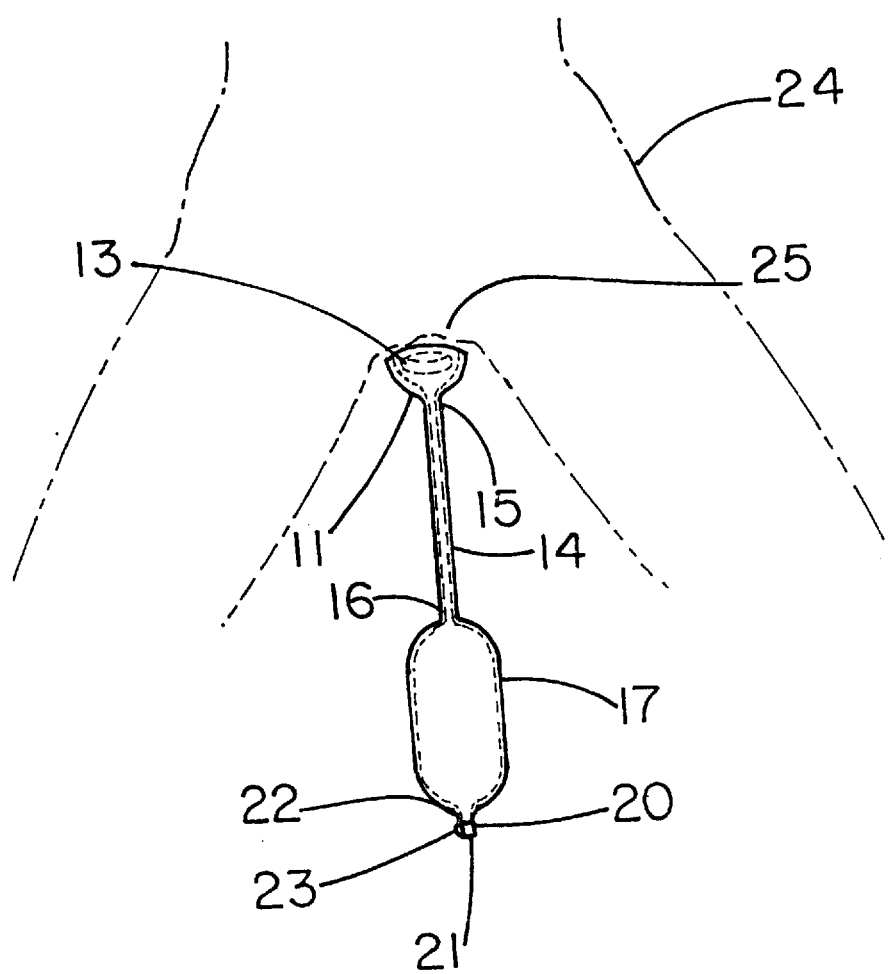
FIG. 2 is a front elevational view of the present invention.

With reference now to the drawings, and in particular to FIGS. 1 through 2 thereof, a new female urine collection device embodying the principles and concepts of the present invention and generally designated by the reference numeral 10 will be described.

As best illustrated in FIGS. 1 through 2, the female urine collection device 10 generally comprises a receiver member 11 being adapted to be positioned between legs of a female person 24. The receiver member 11 is a flexible contortable cup which is adapted to fit over a female's labia 25. An absorbent material 13 having a thickness is removably disposed upon the receiver member 11. The absorbent material 13 is removably received and seated in the flexible contortable cup 11 and is sponge-like.

An elongate flexible tubular member 14 is conventionally connected to the receiver member 11. The elongate flexible tubular member 14 has a first end 15 which is disposed through a side wall 12 of the flexible contortable cup 11 and also has a second end 16. The flexible tubular member 14 has a length of approximately 12 inches. A urine collection member 17 is conventionally connected to the elongate flexible tubular member 14. The urine collection member 17 has a bladder-like container having a first end 18 through which the second end 16 of the elongate flexible tubular member 14 is disposed. The bladder-like container 17 also has a spout 20 being conventionally disposed through a second end 19 thereof and further has a cap assembly being removably attached to the spout 20 and being closable over an opening through the spout 20. The cap assembly includes an eyelet 22 being mounted about the spout 20, and also includes a flexible connector 23 being conventionally attached to the eyelet 22, and further includes a cap member 21 being conventionally connected to the flexible connector 23 and being removably attached over the opening through the spout 20. The bladder-like container 17 is made of plastic. The bladder-like container 17 has a volume of approximately 500 cubic centimeters.

In use, the user fits the receiver member 11 over one's labia 25, and makes sure that the cap member 21 is closed over the opening through the spout 20 before urinating into the receiver member 11 with the urine being collected in the bladder-like container 17.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A female urine collection device comprising:
   a receiver member being adapted to be positioned between legs of a female person;
   an absorbent material being removably disposed upon said receiver member;
   an elongate flexible tubular member being connected to said receiver member;
   a urine collection member being connected to said elongate flexible tubular member; and
   said absorbent material being generally arcuate having a convex side and a concave side, said convex side being positioned adjacent an end of said receiver member when said absorbent material is received by said receiver member whereby said absorbent member is positioned offset from a second end of said receiver member.

2. A female urine collection device as described in claim 1, wherein said receiver member is a flexible contortable cup which is adapted to fit over a female's labia.

3. A female urine collection device as described in claim 2, wherein said elongate flexible tubular member has a first end which is disposed through a side wall of said said second end of said receiver member.

4. A female urine collection device as described in claim 3, wherein said urine collection member is a bladder container having a first end through which a second end of said elongate flexible tubular member is disposed, said bladder container also having a spout being disposed through a second end thereof and further having a cap assembly being removably attached to said spout and being closable over an opening through said spout.

5. A female urine collection device as described in claim 4, wherein said cap assembly includes an eyelet being mounted about the spout, and also includes a flexible connector being attached to said eyelet, and further includes a cap member being connected to said flexible connector and being removably attached over said opening through said spout.

6. A female urine collection device as described in claim 4, wherein said bladder container is made of plastic.

7. A female urine collection device comprising:
- a receiver member being adapted to be positioned between legs of a female person, said receiver member being a flexible contortable cup which is adapted to fit over a female's labia;
- an absorbent material having a thickness and being removably disposed upon said receiver member, said absorbent material being removably received in said flexible contortable cup;
- said absorbent material being generally arcuate having a convex side and a concave side, said convex side being positioned adjacent an end of said receiver member when said absorbent material is received by said receiver member whereby said absorbent member is positioned offset from a second end of said receiver member;
- an elongate flexible tubular member being connected to said receiver member, said elongate flexible tubular member having a first end which is disposed through a side wall of said second end of said receiver member, said flexible tubular member having a length of approximately 12 inches; and
- a urine collection member being connected to said elongate flexible tubular member, said urine collection member being a bladder container having a first end through which a second end of said elongate flexible tubular member is disposed, said bladder container also having a spout being disposed through a second end thereof and further having a cap assembly being removably attached to said spout and being closable over an opening through said spout, said cap assembly including an eyelet being mounted about the spout, and also including a flexible connector being attached to said eyelet, and further including a cap member being connected to said flexible connector and being removably attached over said opening through said spout, said bladder-like container being made of plastic, said bladder-like container having a volume of approximately 500 cubic centimeters.

* * * * *